United States Patent [19]
Singh et al.

[11] Patent Number: 5,223,310
[45] Date of Patent: Jun. 29, 1993

[54] SHEAR SENSITIVE MONOMER-POLYMER LAMINATE STRUCTURE AND METHOD OF USING SAME

[75] Inventors: Jag J. Singh, Yorktown; Abe Eftekhari, Newport News; Devendra S. Parmar, Hampton, all of Va.

[73] Assignee: The United States of America as represented by the Administrator of the National Aeronautics and Space Administration, Washington, D.C.

[21] Appl. No.: 849,612

[22] Filed: Mar. 2, 1992

[51] Int. Cl.$^5$ ............................................ C09K 19/00
[52] U.S. Cl. .................................... 428/1; 428/409; 428/480; 428/913; 359/67; 359/74; 359/82
[58] Field of Search ............... 428/1, 480, 913, 409; 359/66, 70, 67, 93, 105, 82, 74

[56] References Cited

U.S. PATENT DOCUMENTS

| | | | |
|---|---|---|---|
| 3,600,060 | 8/1971 | Churchill | 359/79 |
| 3,872,050 | 3/1975 | Benton | 359/51 |
| 4,232,951 | 11/1980 | Aharoni et al. | 359/43 |
| 4,412,059 | 10/1983 | Krigbaum et al. | 528/192 |
| 4,891,418 | 1/1990 | Hara et al. | 528/195 |
| 5,009,489 | 4/1991 | Eguchi et al. | 359/75 |
| 5,075,043 | 12/1991 | Robello et al. | 252/582 |

FOREIGN PATENT DOCUMENTS 2746228 4/1979 Fed. Rep. of Germany .......... 428/1
83113 5/1984 Japan .

OTHER PUBLICATIONS

Parmar, D. S., "A novel boundary layer sensor utilizing domain switching in ferroelectric liquid crystals", Rev. Sci. Instrum. 62(2), Feb. 1991, pp. 474–479.
de Gennes, P. G., The Physics of Liquid Crystals, Clarendon Press (Oxford), p. 303, 1974.

*Primary Examiner*—Ellis P. Robinson
*Assistant Examiner*—Nasser Ahmad
*Attorney, Agent, or Firm*—Kevin B. Osborne

[57] ABSTRACT

The laminate structure comprises a liquid crystal polymer substrate attached to a test surface of an article. A light absorbing coating is applied to the substrate and is thin enough to permit bonding steric interaction between the liquid crystal polymer substrate and an overlying liquid crystal monomer thin film. Light is directed through and reflected by the liquid crystal monomer thin film and unreflected light is absorbed by the underlying coating. The wavelength of the reflected light is indicative of the shear stress experienced by the test surface.

4 Claims, 7 Drawing Sheets

SHEAR SENSITIVE MONOMER-POLYMER LAMINATE STRUCTURE AND METHOD OF USING SAME

ORIGIN OF THE INVENTION

The invention described herein was made jointly by an employee of the United States Government and contract employees under NASA Contracts. In accordance with 35 U.S.C. 202, the contractors elected not to retain title.

BACKGROUND OF THE INVENTION

1. Technical Field of the Invention

The present invention relates generally to shear stress determination and more particularly to determining shear stress via changes in light wavelengths reflected via a monomer-polymer liquid crystal system.

2. Discussion of the Related Art

Cholesteric liquid crystals, monomers as well as polymers, demonstrate the phenomenon of selective reflection where incident white light is reflected in such a way that its wavelength is governed by the instantaneous pitch of the helix structure of these phases. The helical structure can be modulated by thermodynamic as well as mechanical perturbations, e.g., by changing the temperature or by applying an external stress field. The helix pitch may, however, be compensated for temperature effects, thereby leaving it sensitive only to external shear stress. Because of the high viscosity of liquid crystal polymers (LCPs), the shear stress fields required for helix structure modulation in cholesteric LCPs are very high and therefore LCPs are not good candidates for low shear indicators. Shear sensitive, but temperature insensitive, monomer cholesteric liquid crystals are low viscosity phases and their structure can be modulated by relatively low stress fields. As a result, monomer cholesteric liquid crystals have found application in flow visualization and surface temperature measurement in aerodynamic testing as well as in subsonic and supersonic wind tunnel experiments. Many of these experiments have provided significant qualitative information about the flow field. These experiments have not been so successful in providing quantitative data on the flow parameters, especially when the liquid crystal thin films on model surfaces are exposed directly to the wind flow. The lower viscosity of the monomer liquid crystals combined with the poor wettability of the conventional model surfaces results in the thinning and ultimately washing out of the liquid crystal when exposed to wind flow. As a consequence, the selective reflection characteristics of the model surface on which a monomer cholesteric thin film has been applied become time dependent for a given rate of wind flow.

OBJECTS OF THE INVENTION

It is accordingly an object of the present invention to measure shear forces on an article.

It is another object of the present invention to measure shear forces on an article quantitatively.

It is a further object of the present invention to measure shear stresses on an article surface exposed directly to an air flow.

It is yet another object of the present invention to measure shear forces on an article while maintaining sufficient wettability for a shear sensitive monomer liquid crystal overlying the article.

Other objects and advantages of the present invention are apparent from the drawings and specification of the present invention.

SUMMARY OF THE INVENTION

The foregoing and additional objects are obtained by a shear sensitive laminate structure and method of using the same according to the present invention. The laminate structure comprises a liquid crystal polymer substrate attached to a test surface of an article. A light absorbing coating is applied to the substrate and is thin enough to permit bonding steric interaction between the liquid crystal polymer substrate and an overlying liquid crystal monomer thin film. Light is directed through and reflected by the liquid crystal monomer thin film whereas unreflected light is absorbed by the underlying coating. The wavelength of the reflected light is indicative of the shear stress experienced by the test surface.

DETAILED DESCRIPTION OF THE INVENTION

The molecular chirality and an associated macroscopic twist are the two basic characteristics of a cholesteric liquid crystal order. Together they produce a helix structure whose pitch p is typically a few wavelengths of visible light. Selective reflection is a unique feature of the helix structure and occurs when the optical pathlength (np) equals the wavelength ($\lambda$) of the incident light, i.e., $\lambda = np$, where n is the average refractive index of the liquid crystal. Birefringence ($\Delta n = n_e - n_o \sim 0.2$), a characteristic property of a system of long linear molecules, does not allow the wavelength ($\lambda_s$) of the selective reflection to be sharp. Consequently for an incident white light a reflected light bandwidth $\Delta\lambda = p(n_e - n_o) = (\Delta n/n)\lambda$, where $n_e$ and $n_o$ are the refractive indices parallel and perpendicular, respectively, to the molecular director in the same plane, is observed. For a shear sensitive cholesteric liquid crystal, it is known that the pitch of the helical texture normally follows an inverse shear stress dependence as is evident from recent selective reflection measurements. When the shear stress is increased the gradual winding of the helix is visualized in reflection as a dramatic color change from red to blue for an incident white light.

The present invention utilizes the selective reflection properties of a shear sensitive monomer liquid crystal thin film overlying an upper surface of a liquid crystal polymer substrate. Wavelength $\lambda_s$ for the selected reflection from the system is determined by measuring the intensity of the reflected light from the liquid crystal free surface as a function of the air flow differential pressure $\Delta P$.

Figure 1:
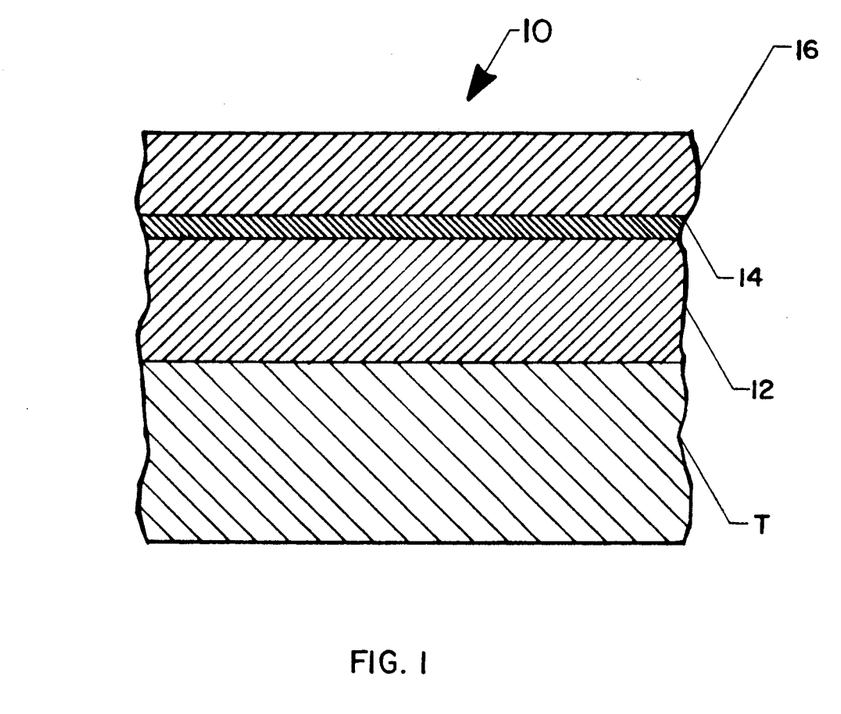
FIG. 1 is a side view of the monomer-polymer liquid crystal laminate according to the present invention.

Referring to FIG. 1, a monomer-polymer liquid crystal (MPLC) laminate structure 10 is seen to comprise flat substrate 12 of liquid crystal polymer (LCP) formed on a test surface of an article T. The upper surface of the LCP substrate 12 is coated with a light absorbing black coating 14. A monomer cholesteric liquid crystal (MLC) thin film 16 overlies the coating 14. This laminate structure 10 is discussed in greater detail below.

A LCP flat substrate 12 was made by the process of injection molding. The embodiment tested and discussed below used XYDAR® SRT-800 brand LCP high strength resin, which is a wholly aromatic liquid crystal proprietary polyester made by Amoco Performance Products, Inc. and trademarked and distributed by Dart Industries, Inc. The XYDAR® SRT-800 brand LCP can be formed into a plastic having a strength approaching steel but a weight as light as aluminum and having a high melting point >350° C. Such a high performance LCP has shown stronger liquid crystallinity of the polymer chain orientation on the surface than in the bulk formed during the process of molding. The LCP substrate is affixed to a test surface of article T by any suitable means such as clamps, adherands, tape, etc.

VECTRA® A130 LCP high strength resin, which is a wholly aromatic liquid crystal polyester distributed by Vectra, Inc., was also investigated as a possible candidate for the substrate but was not selected because of its inadequate wettability with the overlying monomer layer.

Figure 2:
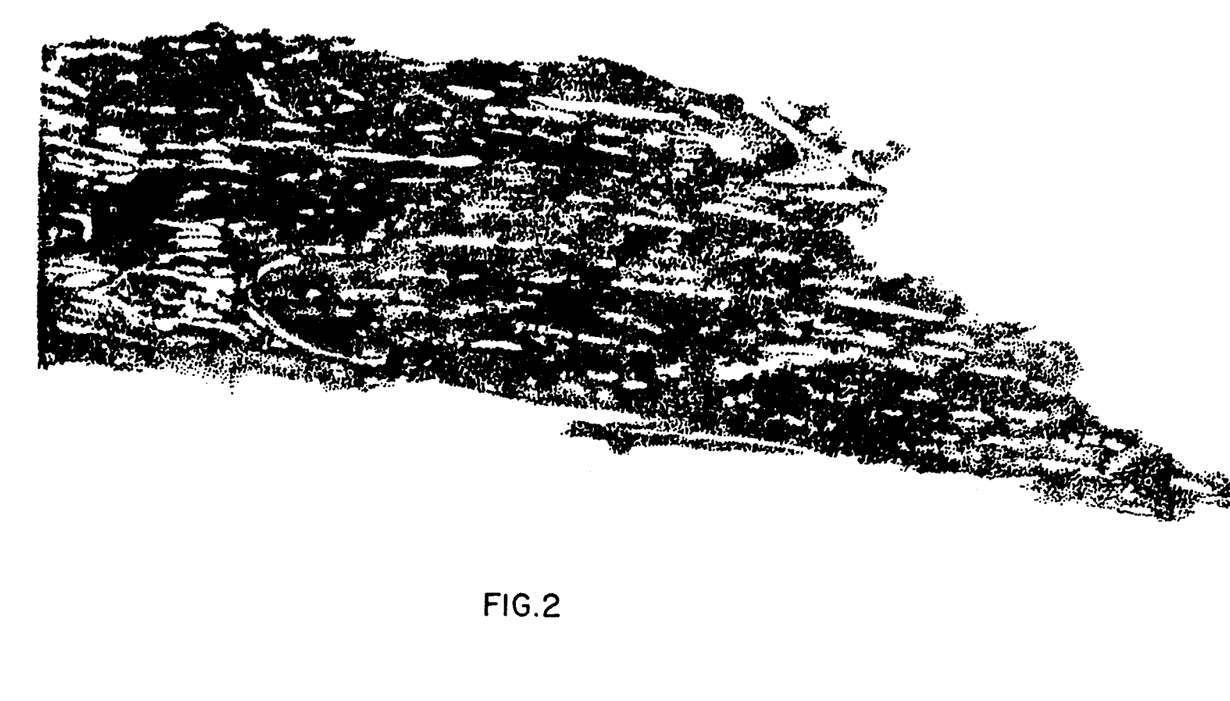
FIG. 2 is a drawing of a surface texture micrograph of an injection molded liquid crystal polymer substrate used in the present invention viewed in reflection with polarizers crossed and an objective magnification of 4×.

As the LCP is molded from the resins in the form of globules, surface orientation of the polymer chains becomes visible in the form of a planar aligned texture. The LCP being opaque, its free surface texture was examined in reflection under crossed polarizers on an optical polarizing microscope such as Optihot-Pol brand microscope, available from Nikon. A particularly preferred optical arrangement is described in D. S. Parmar, Rev. Sci. Instruments, 62, 474 (1991). The micrograph of the surface texture of an LCP surface under crossed polarizers is shown in FIG. 2 where the direction of the polarizer is along the horizontal striations. The black color of the texture clearly demonstrates the liquid crystalline order of molecular orientation on the surface. The remarkable feature of the texture is the presence of the alignment defects in the shape of parabolas. Furthermore, a series of faint cross lines indicate a strong cross-linkage of the polymer main chains and the side chains even on the surface of this material.

The LCP substrate upper surface was coated with flat, black lacquer spray paint in order to absorb the unreflected light. The black coating 14 is thick enough to absorb light which is unreflected by the monomer liquid crystal film 16, but also thin enough to maintain strong steric interactions between the LCP and the overlying monomer cholesteric liquid crystal thin film 16 ($\sim 20$ $\mu$m) applied over the black coating. The absorbing coating increases the contrast of the reflected light and reduces the signal to noise ratio. The particular black paint used in the described embodiment is BB-G1, marketed by Hallcrest, Inc.

The polymer chain orientations on the upper surface of LCP substrate 12 are expected to induce adequate wettability as well as formation of a stable Grandjean texture in the overlying monomer liquid crystal thin film 16 due to surface steric interactions. The particular monomer is a shear sensitive cholesteric liquid crystal TI 511 available from E. M. Industries of New York.

Figure 3A:
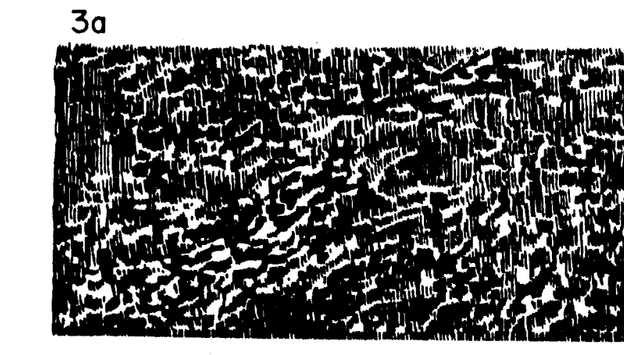
FIG. 3(a) is a drawing of the micrograph of a monomer liquid crystal thin film mounted directly on a liquid crystal polymer substrate of FIG. 2 viewed under the preceding conditions except that the objective magnification is 40×.

The monomer-polymer liquid crystal (MPLC) laminate structure 10 thus obtained was investigated by reflection polarization microscopy. The MPLC laminate free surface texture, shown in the micrograph representation of FIG. 3(a), clearly demonstrates a strong planar orientation, i.e., a Grandjean texture, of the monomer liquid crystal. Since no other surface treatment has been used for the monomer alignment on the LCP substrate, the planar orientation of the monomer is induced purely by the liquid crystalline order on the monomer-polymer interface.

Figure 3B:
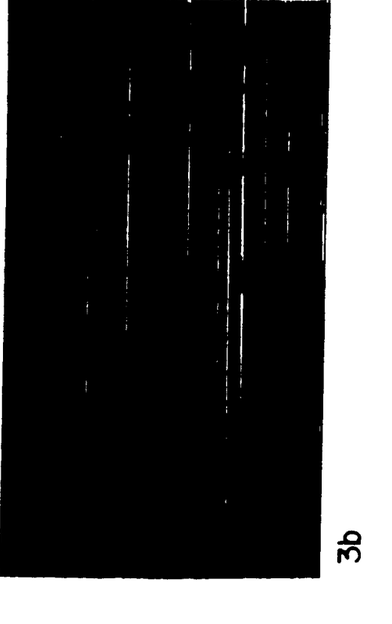
FIG. 3(b) is a drawing of the micrograph of FIG. 3(a) wherein the color changes from red to yellow due to air impingement in the direction of the arrow having a force of approximately 65 mmHg.
Figure 3C:
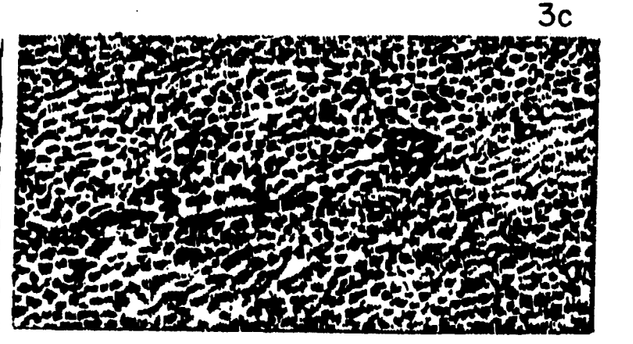
FIG. 3(c) is a drawing of a free surface texture micrograph of a monomer liquid crystal thin film mounted on a blackened metal surface with no force, viewed in reflection with the polarizers crossed and an objective magnification of 40×.
Figure 3D:
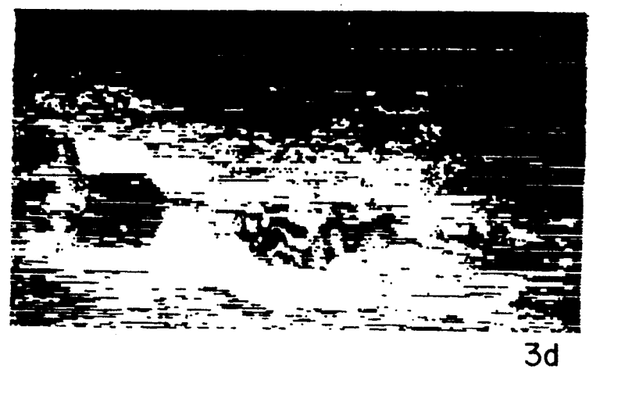
FIG. 3(d) is a drawing of the micrograph of FIG. 3(c) wherein a continuous air flow in the direction of the arrow and having a force of approximately 65 mmHg washes the monomer out of the monomer liquid crystal surface.

The free surface of the monomer liquid crystal is exposed to air field from a small jet in the plane of the monomer-polymer interface along the direction of the polymer chains on the LCP surface, as discussed below in reference to FIG. 4. The black crosses on the monomer liquid crystal (MLC) surface in FIG. 3(a) disappear as the air jet flows on the surface in the direction of the arrow shown in FIG. 3(b). The shear stress (F$\sim$65 mmHg) due to the air impingement changes the reflection color from copper red toward yellow. The MLC texture applied directly on a metal surface per conventional methods in the absence and in the presence of a shear stress F is shown in the micrographs of FIGS. 3(c) and 3(d) respectively. Two distinct features of the texture in FIGS. 3(c,d) in comparison to FIGS. 3(a,b) are: (i) for F=0, the Grandjean texture of FIG. 3(c) on a metal surface is not as good as that of FIG. 3(a) for the LCP surface; and (ii) the liquid crystal is washed out of the substrate surface due to continuous flow of air as evident from the appearance of the black coating on the metal surface in FIG. 3(d). As a result of this material flow, the reflected light intensity becomes time dependent creating lack of definite information on flow visualization. It should also be noted here that, because of the lack of steric interactions on the metal surface, the texture of MLC changes from Grandjean to focal conic soon after the shear stress is removed, thereby making the results irreversible.

Figure 4:
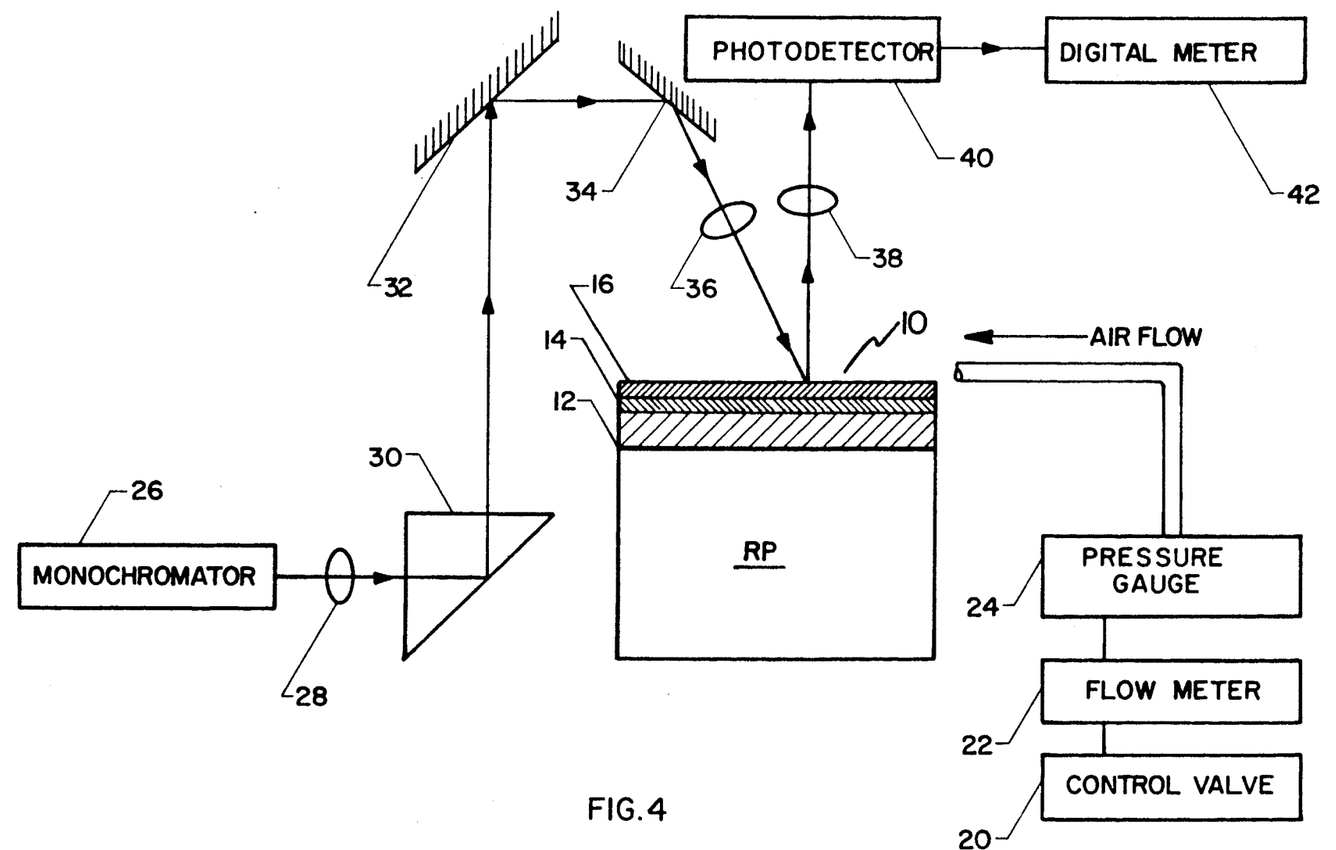
FIG. 4 is a schematic of an experimental setup according to the present invention.

The shear sensitivity of the MPLC system according to the present invention was measured with the experimental system whose schematic diagram is given in FIG. 4. The MPLC laminate 10 comprised of the XYDAR® SRT-800 brand LCP substrate 12 (~5 cm×5 cm), a thin black coating 14 as described and the monomer liquid crystal thin film 16 TI 511 (~20 μm), is mounted in the horizontal plane on a rigid platform RP. An air jet is directed through a standard system comprising a control valve 20, a flow meter 22 and a pressure gauge 24 and is allowed to impinge parallel to the plane of the MLC thin film 16. Light from a microprocessor controlled monochromator 26, such as a Digikron 240 commercially available from CVI Laser Corporation and having a spectral resolution of 0.6 Å, is passed through an appropriate optical system comprising, e.g., a focusing lens 28, a right angle prism 30, two plane mirrors 32 and 34, and a focusing lens 36. The light is incident on the MPLC laminate 10 at an angle of approximately 15° from the normal to the plane of shear. Light intensity reflected normal to the monomer-polymer interface passes through a focusing lens 38 and is detected with a photodetector 40 connected to a digital meter 42. In this way the light due to normal, i.e., specular, reflection from the liquid crystal surface is isolated from reaching the photodetector 40. By adjusting the photodetector aperture and the slit width of the monochromator, the reflection intensity from a sample area of ~0.2 cm×0.5 cm is measured as a function of the air flow differential pressure (ΔP) and the wavelength (λ) of the incident light.

Figure 5A:
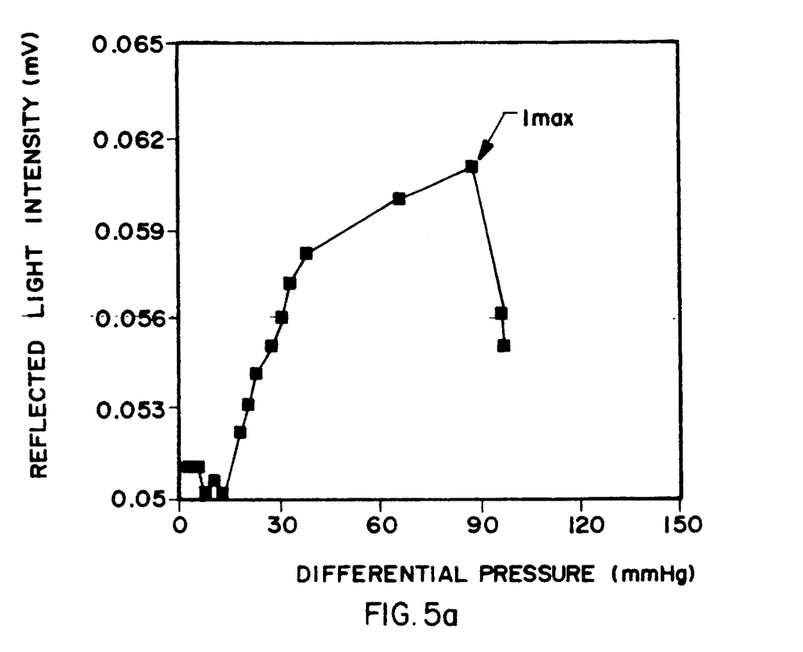
FIG. 5(a) graphs the variation of reflected light intensity of a monomer-polymer liquid crystal laminate according to the present invention as a function of gas flow differential pressure wherein $\lambda = 580$ nm.
Figure 5B:
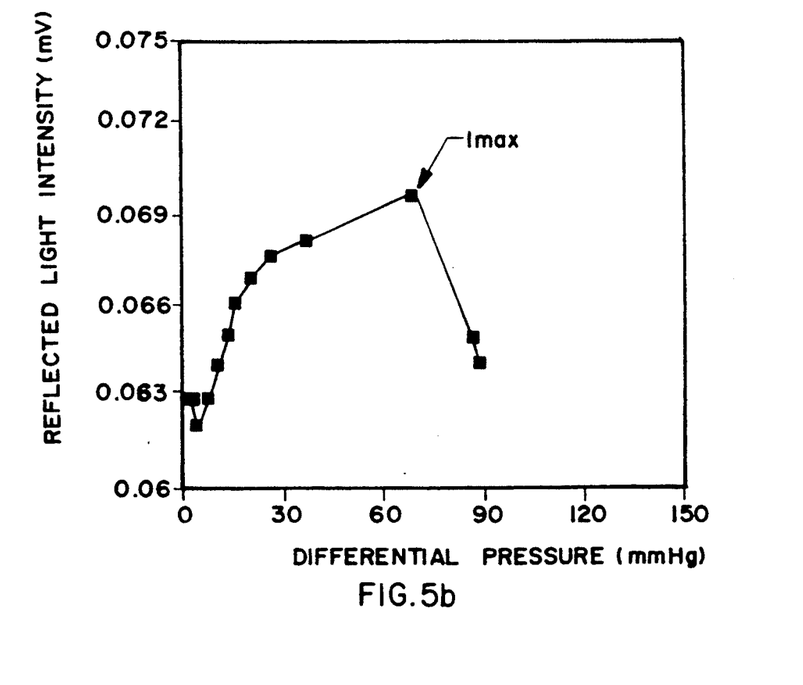
FIG. 5(b) is a graph similar to FIG. 5(a) except that $\lambda = 600$ nm.
Figure 6:
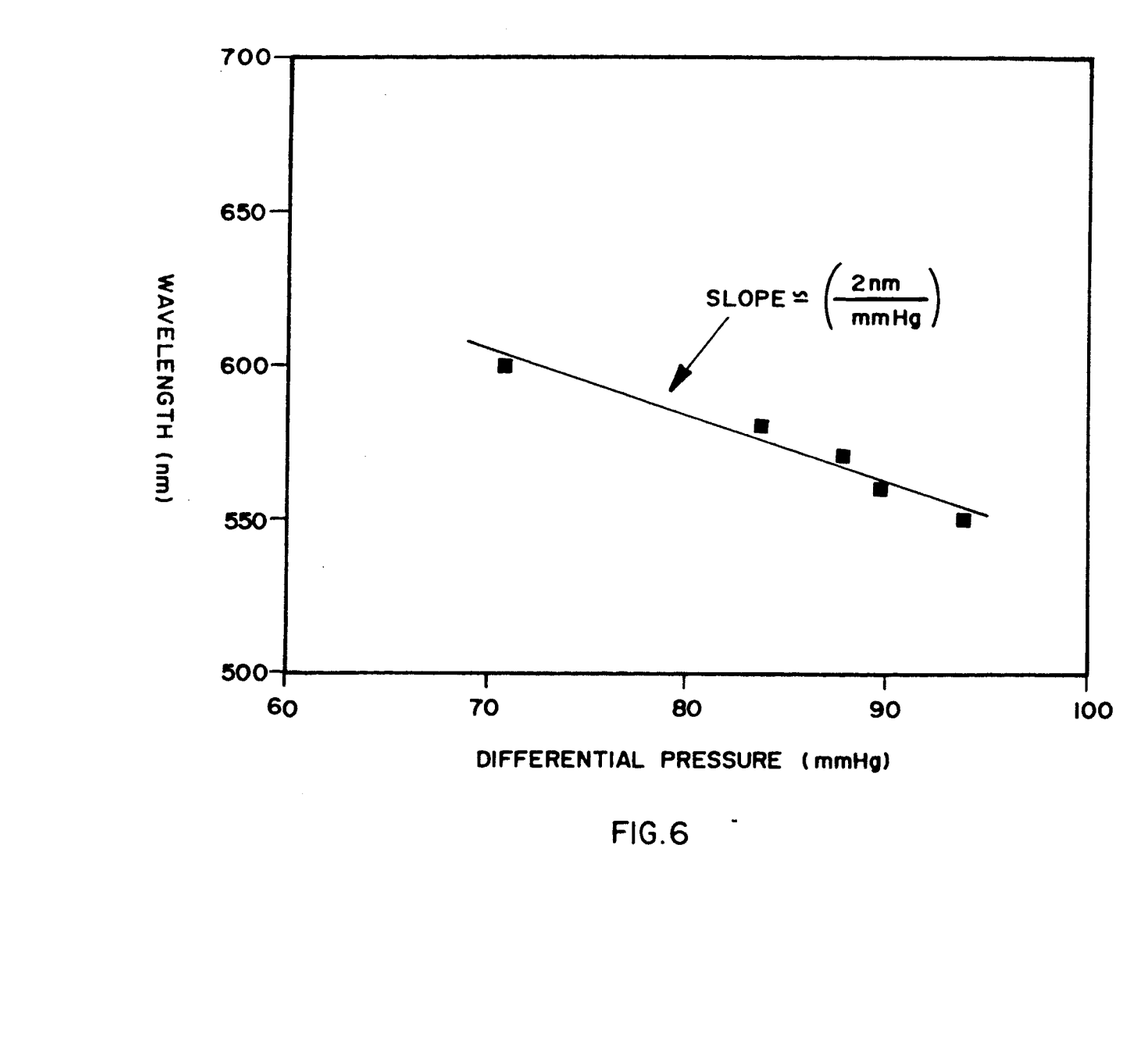
FIG. 6 is a graph of the linear relationship between the reflected wavelength and differential pressure.

Typical variations of the reflected light intensity as a function of the gas flow differential pressure at two wavelengths of 580 nm and 600 nm are shown in FIG. 5(a) and 5(b) respectively. In both cases, the reflected light intensity (I) increases as the gas flow differential pressure (ΔP) is increased from zero. For each wavelength λ, I attains a maximum value at a certain ΔP beyond which it falls rapidly. For a given ΔP, the wavelength $\lambda_s$ corresponding to the maximum value $I_{max}$ in ΔP versus I curve is the wavelength for the selective reflection. For the range of applied differential pressures used in the present application, the ΔP corresponding to the peak in I decreases linearly as the wavelength λ increases. For example, for λ=580 nm in FIG. 5(a), the peak in I was observed at 84 mmHg whereas for λ=600 nm, it was observed at 71 mmHg. Accordingly, a series of relationships between ΔP and peak intensities for specific wavelengths are determined. These predetermined measurements of the peak intensity as a function of ΔP at known wavelengths allow a determination of the wavelength $\lambda_s$ of the selective reflection as a function of the applied differential pressures, as shown in FIG. 6. The variation of $\lambda_s$ with ΔP is linear with a slope of ~2 nm/mmHg. Of course, the particular curves shown by example in the Figures can be stored in a computer and comparisons made with a test wavelength to determine pressure and shear stress on-line.

Figure 7A:
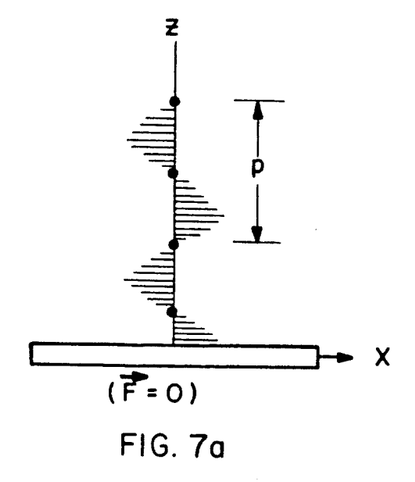
FIG. 7(a) is a geometrical representation of the helical structure of the free surface of the monomer liquid crystal with no force in the X-direction.
Figure 7B:
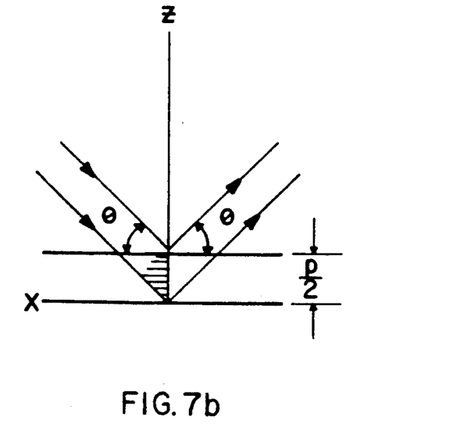
FIG. 7(b) is a representation of light waves reflected by the structure of FIG. 7(a)
Figure 7C:
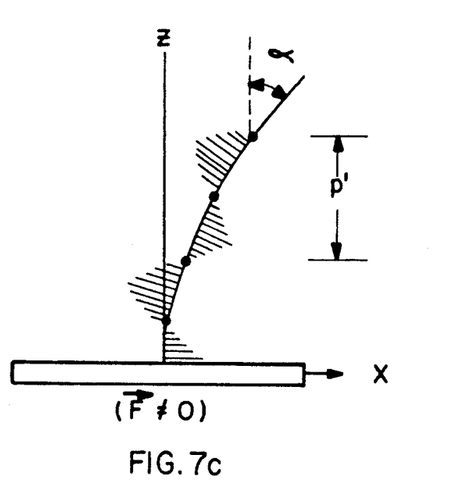
FIG. 7(c) is similar to FIG. 7(a) except that a force is exerted in the X-direction.
Figure 7D:
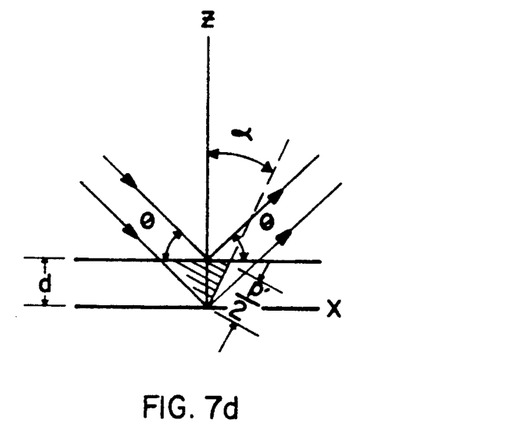
FIG. 7(d) is a representation of light waves reflected by the structure of FIG. 7(c).

The mechanism of the selective reflection from the free surface of the liquid crystal may be understood from the geometrical representation of the helical structure in FIGS. 7(a)–(d). Referring to FIG. 7(a), in the Grandjean texture the helix is aligned along the z-axis, the normal to the surface of planar orientation in the x-y plane. Light of wavelength $\lambda_s$ incident obliquely on the surface is selectively reflected according to the relation p sin θ = $\lambda_s$ as shown in FIG. 7(b), where p is the pitch length of the helix and θ is the angle of reflection. If a force F is applied along the x-axis as shown in FIG. 7(c), then in the limit when the force is small so that the helix tilts by an angle α without deformation, the condition for selective reflection according to FIG. 7(d) is given by p cos α sin θ = $\lambda_s'$, where $\lambda_s'$ is the new wavelength of selective reflection and p cos α = p' is the apparent pitch seen by the incident light. Under the condition of small α, $\lambda_s' < \lambda_s$. For a well defined angle of incidence and angle of viewing the shift ($\lambda_s - \lambda_s'$) can be calculated as:

$$\lambda_s - \lambda_s' = (p/2)\alpha^2 \sin \theta. \tag{1}$$

The director equation of motion for a shear stress F applied along x can be given by the comparison of the elastic and the viscous torques. From these calculations, the tilt α is written as:

$$\alpha = (\eta/Kq_0^2 d)V_x \tag{2}$$

where d is the sample thickness, η is the coefficient of viscosity of the liquid crystal, K is the elastic constant related to the helix tilt, $q_0 = 2\pi/p$ is the helix wavevector and $V_x$ is the director velocity along x due to F. Assuming that F is large enough to force the helix to tilt and the director velocity is proportional to the velocity of the gas due to the differential pressure ΔP, $V_x$ from Torricelli's theorem and Bernoulli's equation governing the flow of fluid through a jet, is given by:

$$V_x = A(2\Delta P/\rho)^{\frac{1}{2}} \tag{3}$$

where A is the constant of proportionality related to the skin friction and ρ is the density of the air. Substitution of $V_x$ from equation (3) in equation (2) results in:

$$\alpha = A\eta(2\Delta P/\rho)^{\frac{1}{2}}(Kq_0^2 d). \tag{4}$$

From equations (1) and (4), the wavelength $\lambda_s'$ of selective reflection corresponding to the air flow differential pressure ΔP can be calculated to be:

$$\lambda_s' = \lambda_s - \{2\pi A^2\eta^2/(K^2 q_0^5 d^2 \rho)\}\Delta P. \tag{5}$$

Equation (5) is the equation defining the linear variation of the selective reflection wavelength as a function of the air differential pressure (ΔP) in FIG. 5. The quantity in the { } brackets of equation (5) is the slope (~2 nm/mmHg) of the line in FIG. 6. Thus equation (5) for $\lambda_s'$ in terms of ΔP can be written as:

$$\lambda_s' = \lambda_s - \beta\Delta P \tag{6}$$

i.e., $$(\lambda_s - \lambda_s')/\beta = \Delta P \tag{7}$$

where the constant β is the slope of the line in FIG. 6. Equation (6) is the equation of the linear variation of the wavelength with ΔP.

Characteristics of a liquid crystal system, comprised of a shear sensitive cholesteric monomer liquid crystal thin film coated on a liquid crystal polymer substrate, have been described. The system provides stable Grandjean texture, a desirable feature for shear stress measurements using selective reflection from the monomer liquid crystal helix structure. Impingement of gas or air flow on the monomer liquid crystal free surface changes the wavelength of the selective reflection for an incident white light from red toward blue with increase in the rate of gas flow. The contrast of the selectively reflected light improves considerably by providing a thin, light absorbing black coating at the monomer-polymer interface. The coating thickness is such that the steric interactions are still sufficiently strong to maintain Grandjean texture. For a small angle of incidence ($\sim 15°$) of a monochromatic light, the measurement of the reflected light intensity normal to the monomer-polymer liquid crystal interface enables a determination of the wavelength ($\lambda_s$) for selective reflection as a function of the gas flow differential pressure ($\Delta P$) applied in the plane of the interface. In the range of the $\Delta P$ (0–100 mmHg) used in the present invention, the variation of $\lambda_s$ with $\Delta P$ is linear with a slope $\sim 2$ nm/mmHg. Furthermore, the shear stress effects are reversible unlike for monomer liquid systems used so far for flow visualization on wind-tunnel surfaces. Thus the present invention offers a suitable method for direct on-line measurement of shear stress field from measurement $\lambda_s$ for an incident white light.

Many modifications, substitutions, and improvements will be apparent to the skilled artisan without departing from the spirit and scope of the present invention as described herein and defined in the following claims.

We claim:

1. A shear sensitive laminate structure for use in determining the shear stress of an article comprising:
    a liquid crystal polymer substrate located on the article;
    a light absorbing coating on an upper surface of said liquid crystal polymer substrate;
    a liquid crystal monomer thin film overlying said coating,
    wherein light directed into said liquid crystal monomer thin film is reflected thereby, wherein the wavelength of the reflected light is indicative of the shear stress experienced by the article; and
    wherein said light absorbing coating absorbs light unreflected by said liquid crystal monomer thin film; and
    wherein said coating is thin enough to permit steric interaction between said liquid crystal polymer substrate and said liquid crystal monomer thin film to maintain Grandjean texture, whereby said film is held in place.

2. The shear sensitive laminate structure according to claim 1, wherein said light absorbing coating comprises a lacquer paint.

3. The shear sensitive laminate structure according to claim 1, wherein said light absorbing coating is black.

4. The shear sensitive laminate structure according to claim 1, wherein said liquid crystal polymer substrate comprises a wholly aromatic polyester.

* * * * *